(12) United States Patent
Kong et al.

(10) Patent No.: US 6,455,225 B1
(45) Date of Patent: Sep. 24, 2002

(54) PHOTORESIST MONOMERS HAVING STABILITY TO POST EXPOSURE DELAY, POLYMERS THEREOF AND PHOTORESIST COMPOSITIONS CONTAINING THE SAME

(75) Inventors: Keun Kyu Kong, Kwangju; Jae Chang Jung, Kyoungki-do; Geun Su Lee, Kyoungki-do; Ki Ho Baik, Kyoungki-do, all of (KR)

(73) Assignee: Hyundai Electronics Industries Co., Ltd.

( * ) Notice: Subject to any disclaimer, the term of this patent is extended or adjusted under 35 U.S.C. 154(b) by 36 days.

(21) Appl. No.: 09/640,261

(22) Filed: Aug. 16, 2000

(30) Foreign Application Priority Data

Aug. 17, 1999 (KR) ............................................. 99-33886

(51) Int. Cl.[7] ............................................. G03F 7/004
(52) U.S. Cl. .................... 430/270.1; 430/326; 430/905; 526/271; 526/281; 562/498
(58) Field of Search .............................. 430/270.1, 326; 526/281, 271; 562/498

(56) References Cited

U.S. PATENT DOCUMENTS

| | | | | |
|---|---|---|---|---|
| 4,576,742 A | * | 3/1986 | Sprecker et al. | 252/522 |
| 5,705,503 A | * | 1/1998 | Goodall et al. | 526/281 |
| 6,143,465 A | * | 11/2000 | Choi | 430/270.1 |
| 6,235,447 B1 | * | 5/2001 | Lee et al. | 430/270.1 |
| 6,258,901 B1 | * | 7/2001 | Kaneko et al. | 526/77 |
| 6,322,948 B1 | * | 11/2001 | Jung et al. | 430/270.1 |

FOREIGN PATENT DOCUMENTS

JP 2000-159717 A * 6/2000 ............ C07C/43/317
JP 2000231191 A * 8/2000 ............ G03F/7/038

OTHER PUBLICATIONS

Machine Translation of JP 2000–159717A.*
Chemical Abstract No. 133:51203 & JP 2000159717.

* cited by examiner

*Primary Examiner*—Rosemary Ashton
*Assistant Examiner*—Yvette M. Clarke
(74) *Attorney, Agent, or Firm*—Townsend and Townsend and Crew LLP

(57) ABSTRACT

The present invention provides novel photoresist monomers, and photoresist polymers derived from monomers comprising the same. The photoresist monomers of the present invention are represented by the following formula:

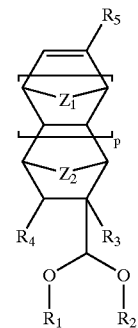

where $Z_1$, $Z_2$, $R_1$, $R_2$, $R_3$, $R_4$, $R_5$ and p are those defined herein. The photoresist compositions comprising the photoresist polymers of the present invention have excellent etching resistance and heat resistance, and remarkably enhanced PED stability (post exposure delay stability).

22 Claims, 4 Drawing Sheets

PHOTORESIST MONOMERS HAVING STABILITY TO POST EXPOSURE DELAY, POLYMERS THEREOF AND PHOTORESIST COMPOSITIONS CONTAINING THE SAME

BACKGROUND OF THE INVENTION

1. Field of the Invention

The present invention relates to photoresist monomers, polymers derived therefrom and photoresist compositions containing such polymers. In particular, the present invention is directed to photoresist polymers and photoresist compositions containing such polymers which are not sensitive to the presence of environmental amine contaminants in a lithography process (e.g., using an ultraviolet light source) when fabricating a minute circuit for high integration semiconductor devices, and processes for preparing such photoresist polymers and photoresist compositions.

2. Description of the Background Art

Use of chemical amplification-type photoresists (i.e., photoresist compositions) is currently being investigated in photolithography processes to achieve a high sensitivity in minute image-formation on semiconductor devices. Such photoresists are generally prepared by blending a photoacid generator with a matrix resin polymer (i.e., photoresist polymer) having an acid labile group.

In a photolithography process for producing semiconductor devices, the resolution of an image depends on the wavelength of the light used. Thus, the shorter the wavelength, higher the resolution, i.e., shorter wavelengths allow smaller pattern formation.

In order to be useful in a photolithography process, a photoresist (PR) must have an excellent etching and heat resistance, and adhesiveness. Moreover, to reduce the cost of manufacturing semiconductor devices, a PR should be capable of being developed in a common developing solution, such as a 2.38 wt % aqueous tetramethylammonium hydroxide (TMAH) solution. These qualities are particularly important in photolithography processes utilizing a short wavelength light source including KrF (248 nm), ArF (193 nm), VUV (157 nm) and EUV (13 nm).

While it is difficult to synthesize a photoresist polymer that satisfies all of these requirements, a variety of photoresist polymers with improved etching resistance, adhesiveness and resolution have been developed. Unfortunately, however, most chemically-amplified photoresists currently available have a relatively short post exposure delay (PED) stability. In general, when there is delay between exposure of the photoresist to light and development of the exposed photoresist, acids that are generated on the exposed area are neutralized by amine compounds which may be present in the production atmosphere. Since the pattern formation depends on acids that are generated by the exposure, neutralization of acids by atmospheric amine compounds reduce, prevent or alter a pattern formation, e.g., a T-topping phenomenon may occur where the top portion of the pattern forms a T-shape.

SUMMARY OF THE INVENTION

It is therefore an object of the present invention to provide a photoresist monomers having an enhanced PED stability.

Another object of the present invention is to provide PR polymers using the PR monomers described above and a process for preparing the same.

Another object of the present invention is to provide photoresist compositions using the PR polymers described above, and a process for preparing the same.

Still another object of the present invention is to provide a semiconductor device produced by using the above described PR composition.

DETAILED DESCRIPTION OF THE PREFERRED EMBODIMENTS

Figure 1:
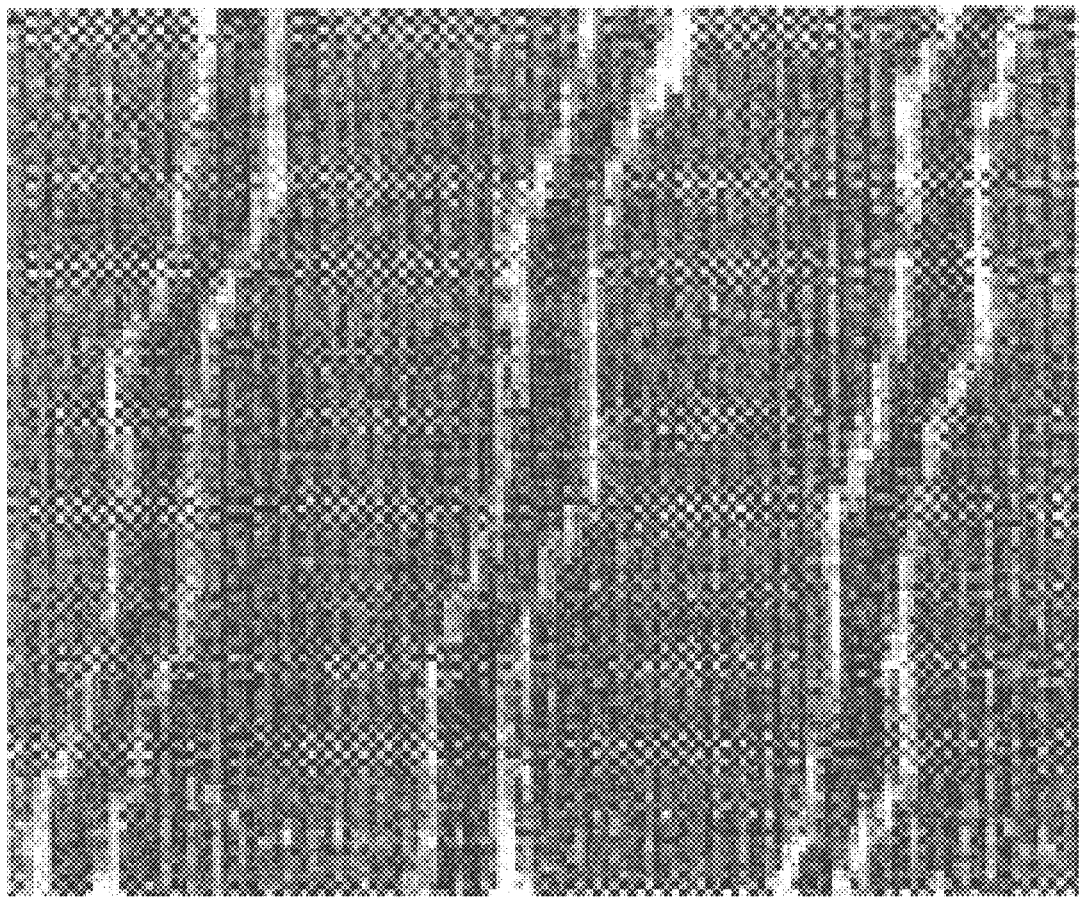
FIG. 1 is a photograph showing a pattern obtained by using photoresist compositions of the present invention without post exposure delay (PED)

The present invention will be described with regard to the accompanying drawings which assist in illustrating various features of the invention. The drawings are provided for the purpose of illustrating the practice of the present invention and do not constitute limitations on the scope thereof.

One aspect of the present invention provides a photoresist monomer of the formula:

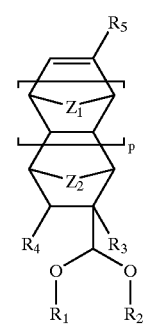

where
- each of $Z_1$ and $Z_2$ is independently $CH_2$, $CH_2CH_2$, O or S;
- each of $R_1$ and $R_2$ is independently substituted or unsubstituted ($C_1$–$C_5$) straight or branched chain alkyl;
- each of $R_3$ and $R_4$ is independently hydrogen, or substituted or unsubstituted ($C_1$–$C_5$) straight or branched chain alkyl;
- $R_5$ is hydrogen or methyl; and
- p is an integer from 0 to 5.

Preferably, the PR monomer of the present invention is selected from the group consisting of compounds of formulas 1a to 1d.

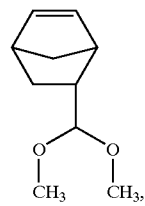

1a

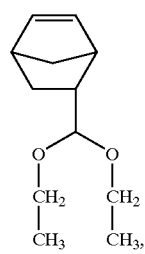

1b

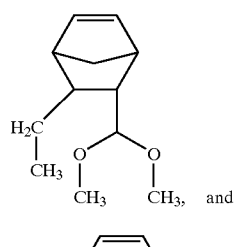  and

1c

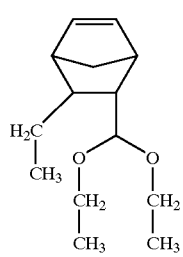

1d

While compounds of formula 1 can be prepared by variety of methods, in one particular embodiment of the present invention, the compound of formula 1, where p is 0, is prepared by:

(a) reacting a compound of the formula:

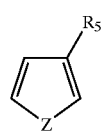

2 with an aldehyde compound of the formula:

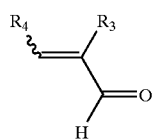

3 to produce a cyclic aldehyde compound of the formula:

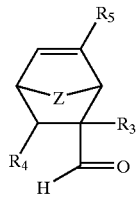

4

(b) reacting the compound of formula 4 with an alcohol in the presence of a catalyst under conditions sufficient to produce the compound of formula 1, where $R_1$, $R_2$, $R_3$, $R_4$ and $R_5$ are those defined above, and Z means $Z_2$.

The process can further include the steps of (c) neutralizing the acid present in the reaction mixture with a base (i.e., alkaline compound).

In one particular aspect of the step (a) of the above described preparation process, the compound of formula 2 is added to an organic solvent and the resulting solution is cooled to temperature in the range of −15 to −25° C. The compound of formula 3 is then added dropwise to the reaction mixture, and the resulting mixture is stirred for 8 to 12 hours. The compound of formula 4 can be obtained by concentrating the reaction mixture and distilling the compound of formula 4 under reduced pressure.

In steps (b) and (c), the compound of formula 4 is reacted with an alcohol (e.g., $R_1OH$, $R_2OH$, or mixtures thereof), preferably with refluxing, in the presence of an acid catalyst. Any acids present in the reaction mixture is then neutralized with an alkaline compound (i.e., a basic compound). The compound of formula 1 which is produced in the reaction can be obtained from the reaction mixture by distillation under reduced pressure. Preferred acid catalysts of the step (b) includes trifluoromethanesulfonic acid is.

The present invention also provides a photoresist polymer derived from a monomer comprising a compound of formula 1. The photoresist polymer can further comprise a second monomer of the formula:

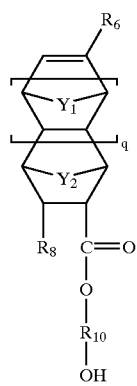

5 where
each of $Y_1$ and $Y_2$ is independently $CH_2$, $CH_2CH_2$, O or S;
$R_6$ is hydrogen or methyl;
$R_8$ is hydrogen, or substituted or unsubstituted ($C_1$–$C_5$) straight or branched chain alkyl;

$R_{10}$ is substituted or unsubstituted ($C_1$–$C_5$) straight or branched chain alkylene; and q is an integer from 0 to 5.

The polymer of the present invention can further comprise a third monomer having an acid labile protecting group. Exemplary acid labile protecting groups include tert-butyl, tetrahydrofuran-2-yl, tetrahydropyran-2-yl, 2-ethoxyethyl and tert-butoxyethyl.

In particular, the compound comprising an acid labile group is preferably a compound of the formula:

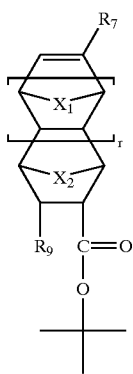

6 where each of $X_1$ and $X_2$ is independently $CH_2$, $CH_2CH_2$, O or S;

$R_7$ is hydrogen or methyl;

$R_9$ is hydrogen, or substituted or unsubstituted ($C_1$–$C_5$) straight or branched chain alkyl; and r is an integer from 0 to 5.

In one particular embodiment, polymers of the present invention is of the formula:

each monomeric units. For example, the total amount "a" of the unit derived from maleic anhydride may be inter dispersed throughout the polymer or it may be concentrated in one particular location of the polymer.

It is believed that one method for improving the PED stability of a photoresist composition is to change the shape of the polymer in the photoresist composition. The method changing the shape of the polymer in the photoresist composition is to use a shear thinning resist. A shear thinning resist can be prepared by (i) using a non-Newtonian shear thinning solvent as a component of the photoresist composition; (ii) changing the structure of the polymer; and/or (iii) controlling the temperature of the photoresist composition while it is being coated on the semiconductor substrate.

Thus, another embodiment of the present invention is directed to preparing the shear thinning resist by changing the structure of the polymer. The polymers of the present invention act as shear thinning agents unlike the conventional photoresist polymers. Without being bound by any theory, it is believed that the polymers of the present invention are a rigid rod or ellipsoidal shape and orient parallel to the shear direction providing a more tightly packed structure with little or no gaps between molecules in the coated layer. It is believed that this tightly packed structure prevents the acid, which is generated in a photolithography process, from being neutralized by the environmental amine. As a result, photoresist polymers of the present invention provide a good photoresist pattern formation even if there is a post exposure delay.

Preferably, the molecular weight of polymers of the present invention is in the range of from about 4000 to about 12000.

Preferred polymers of the present invention include polymers of the formulas 7a and 7b.

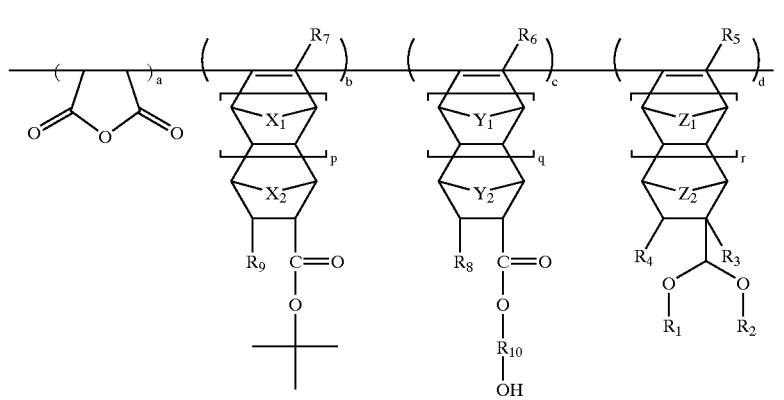

7 where $X_1$, $X_2$, $Y_1$, $Y_2$, $Z_1$, $Z_2$, $R_1$, $R_2$, $R_3$, $R_4$, $R_5$, $R_6$, $R_7$ $R_8$, $R_9$, $R_{10}$, p, q, and r are those defined above; and a, b, c and d represent the relative amounts of each monomers, wherein the mole ratio of a:b:c:d= 0.50:0.125~0.40:0.025~0.10:0.05~0.35.

Each monomeric units in the polymer of formula 7 represents a total relative ratio of each monomers. Thus, the formula 7 is not intended to indicate any particular order of

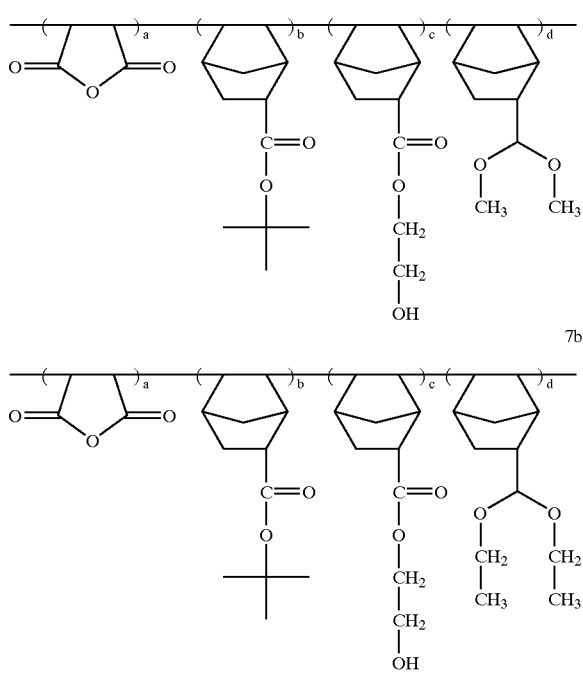

where a, b, c and d are those defined above.

Polymers of the present invention can be prepared by a radical polymerization of monomers with a conventional radical polymerization initiator. An exemplary procedure for preparing polymers of the present invention includes the steps of:

(a) admixing, preferably in an organic solvent,
   (i) a compound of formula 1,
   (ii) a compound of formula 5,
   (iii) optionally a compound of formula 6,
   (iv) maleic anhydride, and
   (iv) polymerization initiator; and
(b) polymerizing said admixture under an inert atmosphere.

The organic solvent suitable for polymerization is selected from the group consisting of tetrahydroluran, toluene, benzene, methylethylketone and dioxane.

Exemplary polymerization initiator include any conventional radical polymerization initiators such as benzoylperoxide, 2,2'-azobisisobutyronitile (AIBN), acetylperoxide, laurylperoxide, tert-butylperacetate, tert-butylhydroperoxide and di-tert-butylperoxide.

The present invention also provides a photoresist composition comprising a photoresist polymer of the present invention, an organic solvent and a photoacid generator.

Preferred photoacid generators include sulfides and onium type compounds. In one particular embodiment of the present invention, the photoacid generator is selected from the group consisting of diphenyl iodide hexafluorophosphate, diphenyl iodide hexafluoroarsenate, diphenyl iodide hexafluoroantimonate, diphenyl p-ethoxyphenyl triflate, diphenyl p-toluenyl triflate, diphenyl p-isobutylphenyl triflate, diphenyl p-tert-butylphenyl triflate, triphenylsulfonium hexafluororphosphate, triphenylsulfonium hexafluoroarsenate, triphenylsulfonium hexafluoroantimonate, triphenylsulfonium triflate and dibutylnaphthylsulfonium triflate. Typically, the amount of photoacid generator used is from about 0.1% by weight to about 10% by weight of the photoresist resin employed. It has been found that when the photoacid generator is used in the amount less than about 0.1%, it lowers photosensitivity of the PR composition, and when the photoacid generator is used in the amount greater than about 10%, it results in a poor pattern formation due to its high absorption of DIN (Deep Ultra Violet).

Exemplary organic solvents suitable in PR compositions of the present invention include methyl 3-methoxypropionate, ethyl 3-ethoxypriopionate, propylene glycol methyl ether acetate, cyclohexanone, 2-heptanone and (2-methoxy)ethyl acetate. The amount of solvent used is preferably in the range of from about 200% to about 800% by weight of the PR resin (i.e., copolymer). This ratio has been found to be particularly useful in obtaining a photoresist layer of a desirable thickness when coated on to a suitable substrate such as a silicon wafer in production of a semiconductor element.

The PR composition prepared by the present invention has an excellent etching resistance, adhesiveness and heat resistance. Also, its remarkably enhanced PED stability makes it very useful as ArF photosensitive film.

Another embodiment of the present invention provides a method for forming the PR pattern as follows: (a) coating the above described photoresist composition on a substrate of semiconductor element to form a photoresist film; (b) exposing the photoresist film to light using a light source; and (c) developing the photoresist film, for example, using an alkaline solution such as 2.38 wt % TMAH solution. Optionally, the photoresist film can be heated (i.e., baked), preferably to temperature in the range of from about 70° C. to about 200° C., before and/or after the step (b).

Exemplary light sources which are useful for forming the PR pattern include ArF (193 nm), KrF (248 nm), VWN (157 nm), EUV, E-beam, X-ray and ion beam. Preferably, the irradiation energy is in the range of from about 1 mJ/cm$^2$ to about 100 mJ/cm$^2$.

The present invention also provides a semiconductor device, which is manufactured using the photoresist composition described above.

Additional objects, advantages, and novel features of this invention will become apparent to those skilled in the art upon examination of the following examples thereof, which are not intended to be limiting.

I. Preparation of Monomers

EXAMPLE 1

Synthesis of a Monomer of Formula 1a

To a 1000 ml round flask was added 1 mole of cyclopentadiene of formula 2a and 100 g of THF. The solution was cooled to −20° C., and 1.2 mole of acrolein of formula 3a was added dropwise. The reaction mixture was stirred for 10 hours, and concentrated using a vacuum evaporator. The resulting residue was distilled under reduced pressure at 40° C. to provide a monomer of formula 4a (yield: 80%, 106 g).

To a 1000 ml round flask was added 106 g of the monomer of formula 4a, 400 g of methanol, and 0.1 ml of trifluoromethansulfonic acid. The mixture was refluxed for 10 hours. Thereafter, the reaction mixture was neutralized to about pH 7 by adding KOH, and distilled under reduced pressure at 50° C. to provide a monomer of formula 1a (yield: 70%, 74 g).

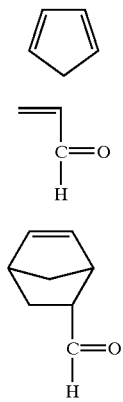

2a

3a

4a

EXAMPLE 2

Synthesis of a Monomer of Formula 1b

The procedure of Example 1 is repeated using ethanol instead of methanol to obtain a monomer of Formula 1b.

II. Preparation of Polymers

EXAMPLE 3

Synthesis of a Polymer of Formula 7a

To a 250 cc flask was added 0.1 mole of maleic anhydride, 0.06 mole of the monomer of formula 6a, 0.01 mole of the monomer of formula 5a, 0.03 mole of the monomer of formula 1a (prepared in Example 1), 0.5 g of AIBN as a polymerization initiator and 20 g of tetrahydrofuran. The mixture was stirred at 65° C. for 10 hours under a nitrogen or an argon atmosphere. Ethyl ether was added to the reaction mixture and the polymer of formula 7a was obtained as a precipitate (yield: 30%, 8.5 g).

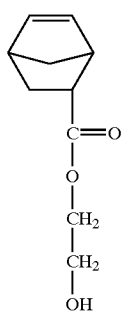

5a

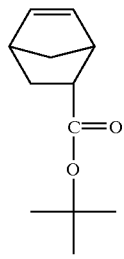

6a

EXAMPLE 4

Synthesis of Polymer of Chemical Formula 7b

The procedure of Example 3 was repeated using the monomer of formula 1b prepared in Example 2 instead of the monomer of formula 1a to obtain a polymer of formula 7b.

III. Preparation of Photoresist Composition and Formation of Pattern

EXAMPLE 5

A photoresist composition was prepared by adding 20 g of the polymer of formula 7a (prepared in Example 3) and 0.24 g of triphenylsulfonium triflate to 160 g of propylene glycol methyl ether acetate.

The composition was coated on a silicon wafer. The coated wafer was soft-baked at 150° C. for 90 seconds, exposed to light using an ArF exposer, post-baked at 140° C. for 90 seconds, and developed in the 2.38 wt % TMAH developing solution to obtain a ultrafine pattern of 0.13 μm L/S.

EXAMPLE 6

The procedure of Example 5 was repeated using the polymer of formula 7b prepared in Example 4 instead of the polymer of formula 7a.

EXAMPLE 7

Experiment of PED Stability

Figure 2:
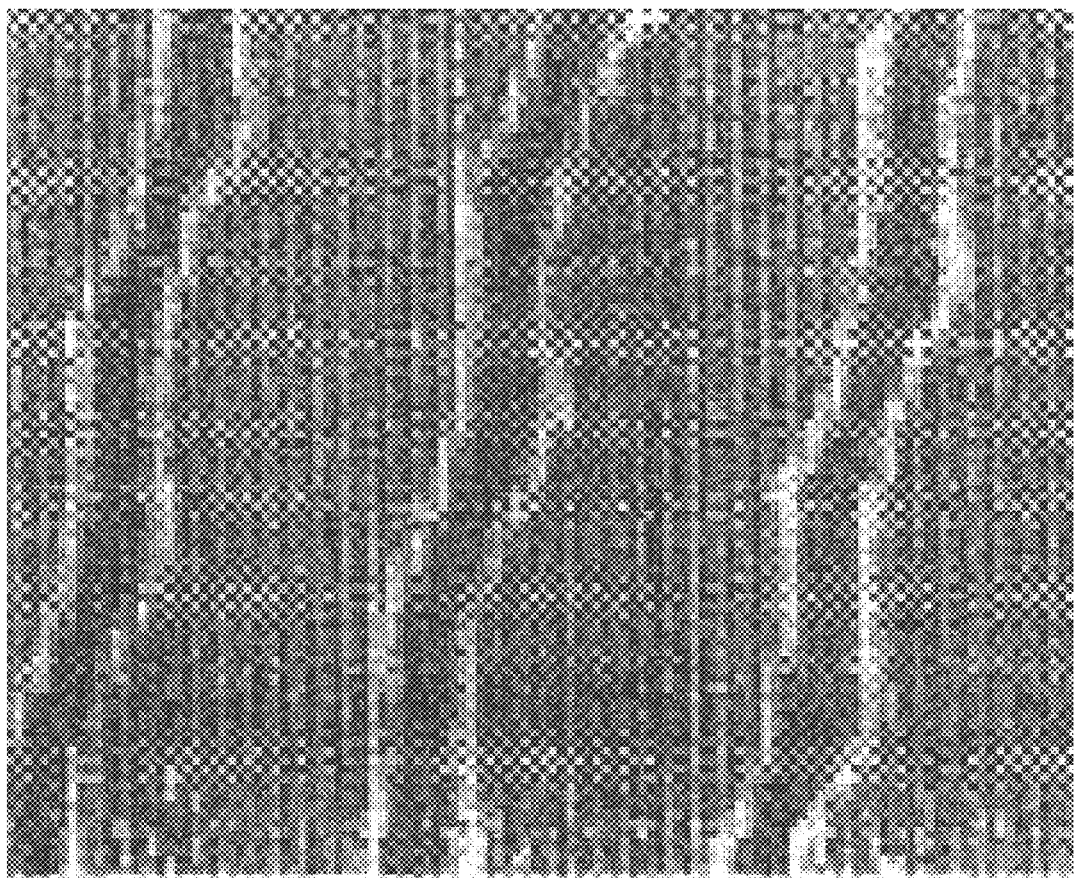
FIG. 2 is a photograph showing a pattern obtained by using photoresist compositions of the present invention and leaving the exposed photoresist compositions for 30 minutes before developing.
Figure 3:
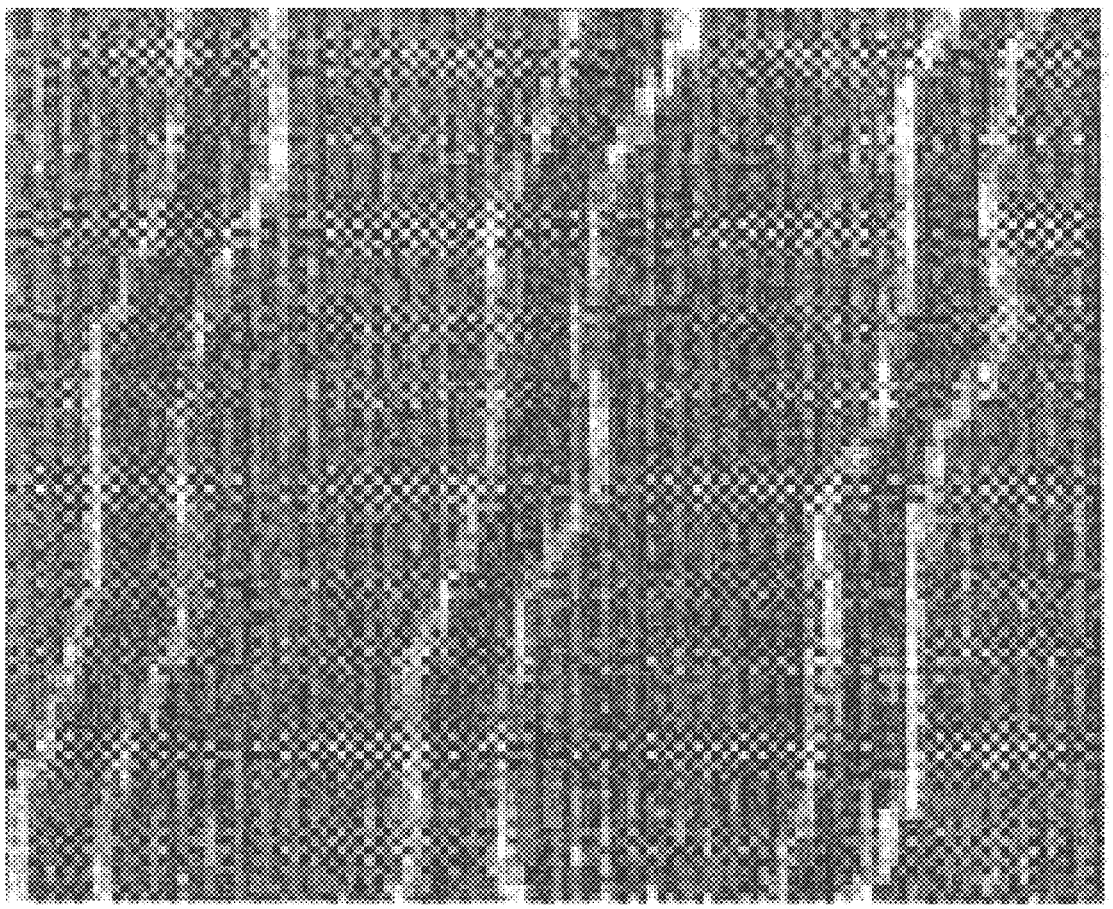
FIG. 3 is a photograph showing a pattern obtained by using photoresist compositions of the present invention and leaving the exposed photoresist compositions for 60 minutes before developing.
Figure 4:
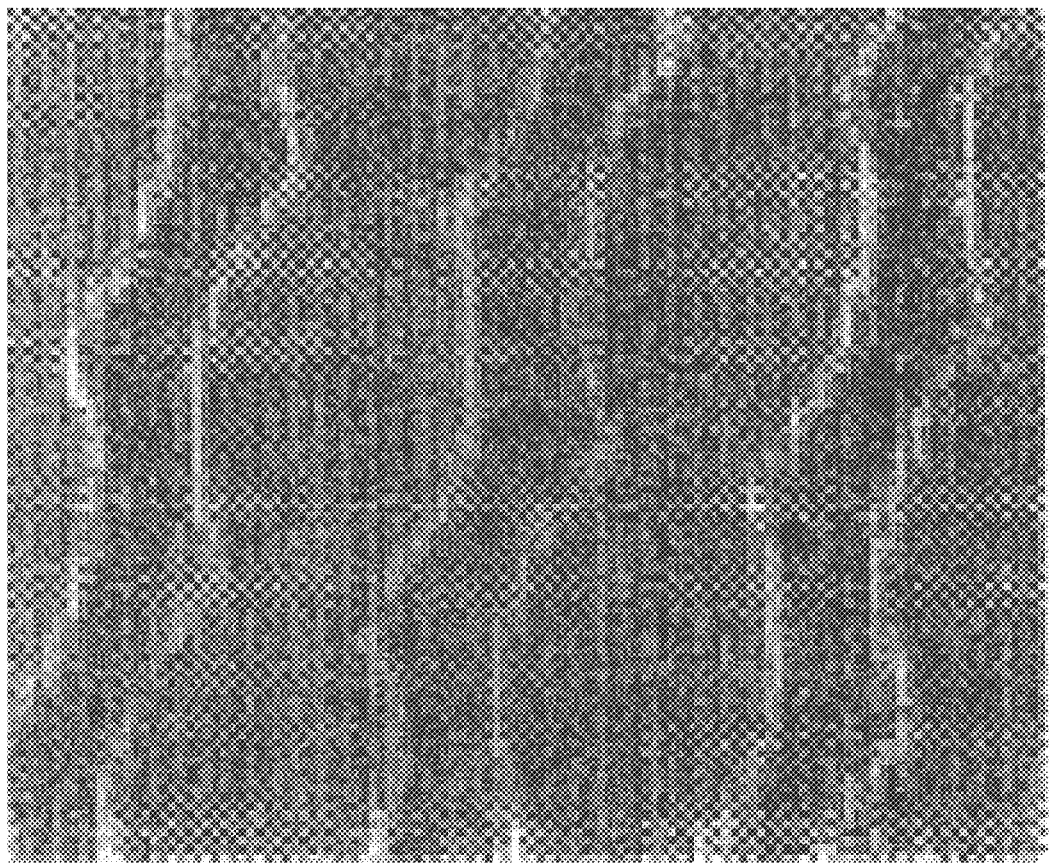
FIG. 4 is a photograph showing a pattern obtained by using photoresist compositions of the present invention and leaving the exposed photoresist compositions for 120 minutes before developing.

In the process of forming a pattern using photoresist compositions prepared in Examples 5 and 6, the exposed silicon wafer was placed in an atmosphere comprising over 30 ppb of amine for 0, 30, 60 and 120 minutes prior to developing the exposed silicon wafer to simulate post-exposure delay. FIGS. 1 to 4 show the results of pattern size variations, and Table 1 shows the variation of critical dimension (CD) resulting from the time delay.

TABLE 1

Variation of critical dimension (CD) resulting from PED.

| Time (min) Polymer | | 0 | 30 | 60 | 120 |
|---|---|---|---|---|---|
| Example 3 (Formula 7a) | CD(nm) 150 nm | 150 | 151 | 153 | 170 |
| Example 4 (Formula 7b) | CD(nm) 150 nm | 151 | 152 | 153 | 169 |
| Polymer without monomer of Formula 1 | CD(nm) 150 nm | 170 (T-top occurred) | *T-top | *T-top | *T-top |

*Pattern is not well formed due to T-top.

As shown in FIGS. 1 to 4 and Table 1, the photoresist composition of the present invention is not sensitive to the presence of environmental amines relative to the conventional photoresist composition. Accordingly, a minute pattern can be formed in spite of post exposure delay.

As discussed above, photoresist compositions of the present invention have excellent PED stability, and as a result are suitable for use in a photolithography process using light sources of the ultrashort wavelength region, such as an ArF (193 nm) light source.

What is claimed is:

1. A photoresist polymer derived from a monomer comprising a compound of the formula:

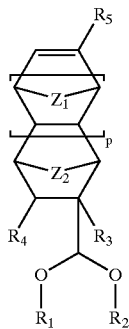

wherein each of $Z_1$ and $Z_2$ is independently $CH_2$, $CH_2CH_2$, O or S;

each of $R_1$ and $R_2$ is independently substituted or unsubstituted ($C_1$–$C_5$) straight or branched chain alkyl;

each of $R_3$ and $R_4$ is independently hydrogen, or substituted or unsubstituted ($C_1$–$C_5$) straight or branched chain alkyl;

$R_5$ is hydrogen or methyl; and p is an integer from 0 to 5, and a compound of the formula:

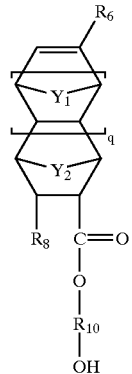

wherein each of $Y_1$ and $Y_2$ is independently $CH_2$, $CH_2CH_2$, O or S;

$R_6$ is hydrogen or methyl;

$R_8$ is hydrogen, or substituted or unsubstituted ($C_1$–$C_5$) straight or branched chain alkyl;

$R_{10}$ is substituted or unsubstituted ($C_1$–$C_5$) straight or branched chain alkylene; and q is an integer from 0 to 5.

2. The photoresist polymer according to claim 1, wherein said monomer further comprises a compound having an acid labile protecting group.

3. The photoresist polymer according to claim 2, wherein said acid labile protecting group is selected from the group consisting of tert-butyl, tetrahydrofuran-2-yl, tetrahydropyran-2-yl, 2-ethoxyethyl and tert-butoxyethyl.

4. The photoresist polymer according to claim 2, wherein said compound having the acid labile protecting group is a compound of the formula:

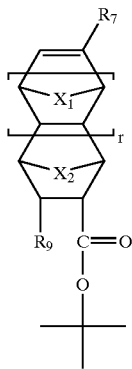

wherein each of $X_1$ and $X_2$ is independently $CH_2$, $CH_2CH_2$, O or S;

$R_7$ is hydrogen or methyl;

$R_9$ is hydrogen, or substituted or unsubstituted ($C_1$–$C_5$) straight or branched chain alkyl; and r is an integer from 0 to 5.

5. The photoresist polymer according to claim 4 of the formula:

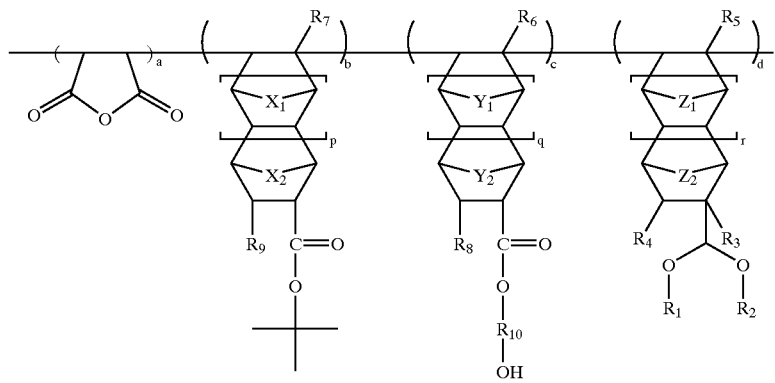
wherein
the mole ratio of a:b:c:d is 0.50:0.125~0.40:0.025~0.10:0.05~0.35.
6. The photoresist polymer according to claim 5 of the formula:
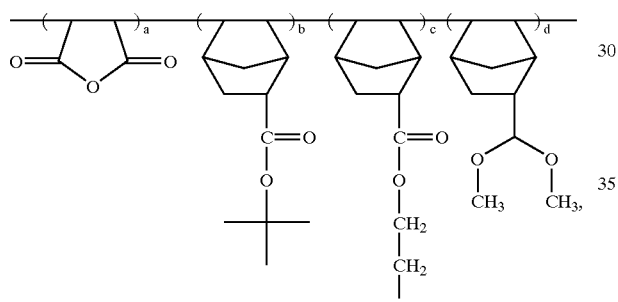
or
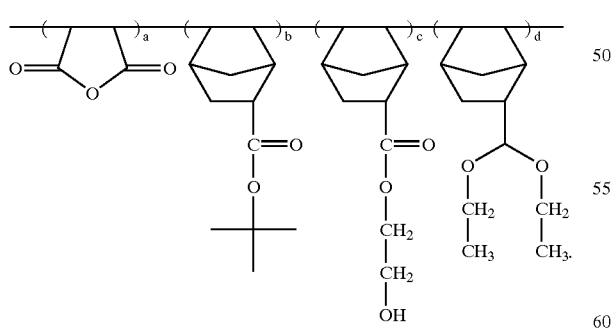
7. A process for preparing said photoresist polymer of claim 5, comprising the steps of:
(a) admixing in an organic solvent
(i) a compound of the formula:
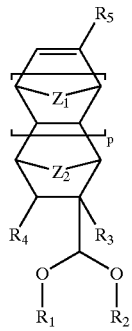
(ii) a compound of the formula:
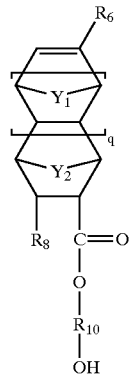
(iii) a compound of the formula:
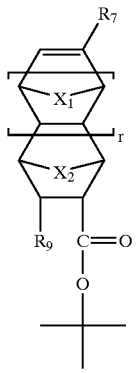

(iv) maleic anhydride, and
(iv) a polymerization initiator; and
(b) polymerizing said admixture under an inert atmosphere.

8. The process according to claim 7, wherein said organic solvent is selected from the group consisting of tetrahydrofuran, toluene, benzene, methylethylketone and dioxane.

9. The process according to claim 7, wherein said polymerization initiator is selected from the group consisting of benzoylperoxide, 2,2'-azobisisobutyronitile (AIBN), acetylperoxide, laurylperoxide, tert-butylperacetate, tert-butylhydroperoxide and di-tert-butylperoxide.

10. The photoresist polymer of claim 1, wherein the molecular weight of said photoresist polymer is in the range of from about 4000 to about 12000.

11. A photoresist composition comprising a photoresist polymer of claim 1, an organic solvent and a photoacid generator.

12. The photoresist composition according to claim 11, wherein said photoacid generator is sulfide or onium type compounds.

13. The photoresist composition according to claim 11, wherein said photoacid generator is selected from the group consisting of diphenyl iodide hexafluorophosphate, diphenyl iodide hexafluoroarsenate, diphenyl iodide hexafluoroantimonate, diphenyl p-methoxyphenyl triflate, diphenyl p-toluenyl triflate, diphenyl p-isobutylphenyl triflate, diphenyl p-tert-butylphenyl triflate, triphenylsulfonium hexafluororphosphate, triphenylsulfonium hexafluoroarsenate, triphenylsulfonium hexafluoroantimonate, triphenylsulfonium triflate and dibutylnaphthylsulfonium triflate.

14. The photoresist composition according to claim 11, wherein said photoacid generator is used in an amount in the range of from 0.1 to 10% by weight of said photoresist polymer employed.

15. The photoresist composition according to claim 11, wherein said organic solvent is selected from the group consisting of methyl 3-methoxypropionate, ethyl 3-ethoxypropionate, propylene glycol methyl ether acetate, cyclohexanone and 2-heptanone.

16. The photoresist composition according to claim 11, wherein the amount of the organic solvent is in the range of from 200 to 800% by weight of said photoresist polymer.

17. A process for forming a photoresist pattern, comprising the steps of:

(a) coating a photoresist composition of claim 11 on a substrate of semiconductor element to form a photoresist film;

(b) exposing said photoresist film to light using a light source; and (c) developing said photoresist film.

18. The process according to claim 17, further comprising a baking step before and/or after said exposure step (b).

19. The process according to claim 18, wherein said baking step is performed at a temperature range of from about 70 to about 200° C.

20. The process according to claim 17, wherein said light source is ArF, KrF, VUV, EUV, E-beam, X-ray or ion beam.

21. The process according to claim 17, wherein said photoresist film is irradiated with light-exposure energy in the range of from 1 to 100 mJ/cm$^2$.

22. A semiconductor element manufactured by the process according to claim 17.

* * * * *

UNITED STATES PATENT AND TRADEMARK OFFICE
CERTIFICATE OF CORRECTION

PATENT NO.   : 6,455,225 B1
DATED        : September 24, 2002
INVENTOR(S)  : Keun Kyu Kong et al.

It is certified that error appears in the above-identified patent and that said Letters Patent is hereby corrected as shown below:

Column 5,
Lines 38-58, figure 7, please replace this figure with the following figure:

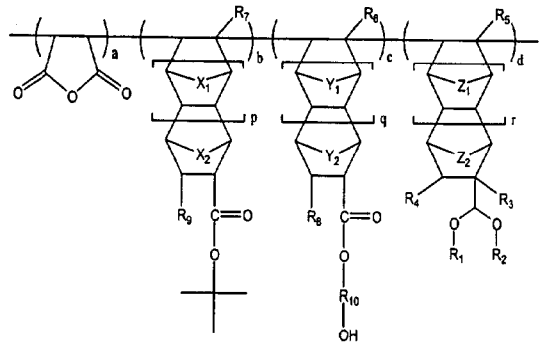

Line 60, please insert a comma followed by a space, after "$R_7$".

Column 7,
Line 45, please replace the word "tetrahydroluran" with the word -- tetrahydrofuran --.
Line 62, please replace the word "p-ethoxyphenyl" with the word
-- p-methoxyphenyl --.

Column 8,
Line 8, please replace the word "DIN" with the word -- DUV --.
Line 39, please replace the word "VWN" with the word -- VUV --.

Signed and Sealed this

Third Day of June, 2003

JAMES E. ROGAN
*Director of the United States Patent and Trademark Office*